United States Patent
Smits et al.

(10) Patent No.: US 10,087,126 B2
(45) Date of Patent: Oct. 2, 2018

(54) PROCESS FOR THE PREPARATION OF HALO-SUBSTITUTED BENZENES

(71) Applicant: SYNGENTA PARTICIPATIONS AG, Basel (CH)

(72) Inventors: Helmars Smits, Stein (CH); Paul Knochel, Muchen (DE); Thomas Klatt, München (DE); Matthias Becker, Gauting (DE)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 15/516,110

(22) PCT Filed: Oct. 8, 2015

(86) PCT No.: PCT/EP2015/073217
§ 371 (c)(1),
(2) Date: Mar. 31, 2017

(87) PCT Pub. No.: WO2016/058895
PCT Pub. Date: Apr. 21, 2016

(65) Prior Publication Data
US 2017/0297981 A1    Oct. 19, 2017

(30) Foreign Application Priority Data
Oct. 14, 2014    (EP) .................................... 14188740

(51) Int. Cl.
C07C 17/25    (2006.01)
C07C 17/383    (2006.01)
C07C 17/35    (2006.01)
C07C 17/38    (2006.01)
C07C 17/013    (2006.01)

(52) U.S. Cl.
CPC ............ *C07C 17/25* (2013.01); *C07C 17/013* (2013.01); *C07C 17/35* (2013.01); *C07C 17/38* (2013.01); *C07C 17/383* (2013.01)

(58) Field of Classification Search
CPC ....... C07C 17/25; C07C 17/38; C07C 17/383; C07C 17/35; C07C 17/013
See application file for complete search history.

(56) References Cited

U.S. PATENT DOCUMENTS
2013/0131016 A1    5/2013    Akama

FOREIGN PATENT DOCUMENTS
EP    1810974 A1    7/2007
GB    2191484 A    12/1987

OTHER PUBLICATIONS

Extended European Search Report for EP14188740.6, dated Mar. 4, 2015.
Unsinn, Andreas et al.: "Directed Magnesiation of Polyhaloaromatics using the Tetramethylpiperidylmagnesium Reagents TMP 2 Mg.2?LiCl and TMPMgCl.LiCl", Advanced Synthesis & Catalysis, vol. 355, No. 8, May 17, 2013 (May 17, 2013), pp. 1553-1560, XP055169619, ISSN: 1615-4150, DOI: 10.1002/adsc.201300185.

(Continued)

*Primary Examiner* — Jafar Parsa

(57) ABSTRACT

The invention relates to a process for the preparation of compound of formula (I) wherein $R_1$ is halogen and $R_2$ is halogen or hydrogen; comprising a) reacting the compound of formula (II) in an aprotic organic solvent in the presence of an aprotic polar co-solvent with a magnesium amide base followed by a halogenating agent, to the compound of formula I wherein $R_1$ is halogen and $R_2$ is hydrogen, and b) reacting the compound of formula (I), wherein $R_1$ is chloro and $R_2$ is hydrogen, in an aprotic organic solvent in the presence of an aprotic polar co-solvent with a magnesium amide base followed by a halogenating agent to a compound of formula I, wherein $R_1$ is chloro and $R_2$ is halogen.

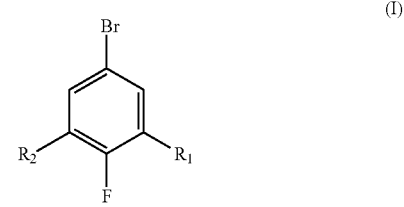

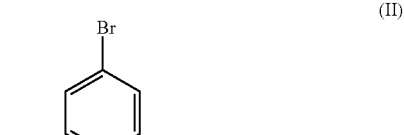

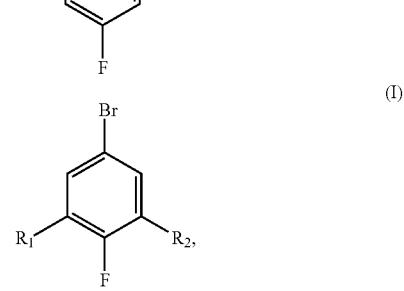

10 Claims, No Drawings

(56) References Cited

OTHER PUBLICATIONS

Prakash, S.G.K. et al: "N-halosuccinimide/BF3-H20, efficient electrophilic halogenating systems for aromatics". In: Journal of the American Chemical Society. American Chemical Society. vol. 126. Jan. 1, 2004 (Jan. 1, 2004). pp. 15770-15776. XP002530032. ISSN: 0002-7863. DOI: 10.1021/JA0465247.
International Search Report and Written Opinion for PCT/EP2015/073217, dated Jan. 26, 2016.

PROCESS FOR THE PREPARATION OF HALO-SUBSTITUTED BENZENES

RELATED APPLICATION INFORMATION

This application is a 371 of International Application No. PCT/EP2015/073217, filed Oct. 8, 2015, which claims priority to EP Application No. 14188740.6 filed Oct. 14, 2014, the contents of which are incorporated herein by reference herein.

The present invention relates to the preparation of halobenzenes of formula I

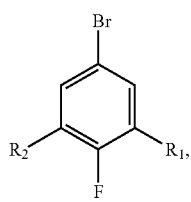

wherein $R_1$ is halogen and $R_2$ is halogen or hydrogen.

Halogenated benzene derivatives of general formula I are useful intermediates for the preparation of biologically active compounds in both pharmaceutical and agrochemical industries as for example described in WO 2009/126668 and WO 2012/173689.

Known synthesis of halobenzenes of a general formula I involve many reaction steps and the introduction of functional groups which allow electrophilic aromatic substitutions in the desired ring positions followed by removal of those groups as for example described in Prakash, G. K. S.; Mathew, T.; Hoole, D.; Esteves, P. M.; Wang, Q.; Rasul, G.; Olah, G. A. J. Am. Chem. Soc. 2004, 126, 15770; WO 2003/099824 and GB 2191484 for 4-bromo-1-fluoro-2-iodo-benzene (Scheme 1).

Scheme 1

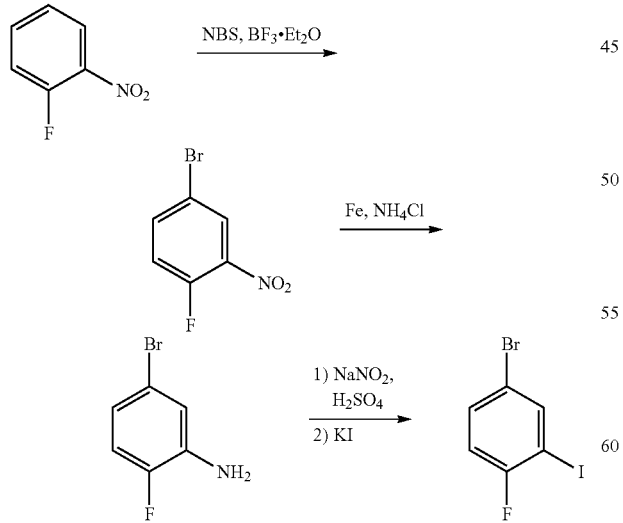

Therefore it would be advantageous to have available a more efficient and more atom economical route to these intermediates. 1-bromo-4-fluoro-benzene would be an ideal starting material producing compounds of a general formula I by selective halogenation adjacent to fluorine atom. The classical electrophilic aromatic halogenation of 1-bromo-4-fluoro-benzene however proceeds with a very low regioselectivity thus producing difficult to separate mixtures of regioisomers and overchlorinated species.

It is therefore the object of the present invention to provide a process for the preparation of compounds of formula I in less reaction steps and with a high regioselectivity.

A potential alternative to electrophilic halogenation would be a selective deprotonation adjacent to the fluorine atom followed by treating the formed anion with a suitable electrophilic halogenating agent. Such deprotonations usually requiring strong lithium bases such as n-butyllithium, lithium diisopropylamide and lithium tetramethylpiperide are well known in the literature (for example US20100041721). However, for a compound of a general formula I, wherein $R_2$ is chloro, despite numerous trials, regioselectivity of deprotonation between the position adjacent to fluorine versus the position between chlorine and bromine are invariably poor (see experimental part). A selective method for further halogenation of polyhalogenated benzenes by deprotonation with magnesium amide bases has been described in Unsinn, A.; Rohbogner, C. J.; Knochel, P. Adv. Synth. Catal. 2013, 355, 1553.

Using TMPMgCl.LiCl (tetramethylpiperidylmagnesium chloride) as magnesium amide base, high selectivity for deprotonation can be achieved. However, a major disadvantage is the use of a base derived from a complex and expensive amine thus increasing considerably complexity and costs of synthesis on a large scale. The use of cheaper and more readily accessible $iPr_2NMgCl.LiCl$ and $Cyhexyl_2NMgCl.LiCl$ for a selective deprotonation of aromatic systems has also been reported. However, the major disadvantage is lower solubility of those bases which requires unfavourably high dilution of the reaction media. Further, in order to achieve high conversion, significant excess of a base has to be used.

Surprisingly, it was found that the addition of an aprotic highly polar co-solvent (relative permittivity above 25) such as HMPA (hexamethylphosphoramide), DMPU (1,3-dimethyl-3,4,5,6-tetrahydro-2(1H)-pyrimidinone) or N,N-tetramethylethylene diamine (TMEDA) to the reaction mixture allows to perform the reaction not only much more concentrated, but also with a significantly increased regioselectivity and overall yield. The present invention allows highly selective deprotonation adjacent to a fluorine atom with a simpler and more readily available base while preserving all the advantages of more complex base described before such as higher concentration, no need for a significant excess of the base, short reaction times and full conversion to the desired product. Additionally, it was found that it is advantageous to perform the process under continuous flow conditions which further reduces the reaction times and excess of reagents.

Thus, according to the present invention, there is provided a process for the preparation of compound of formula I

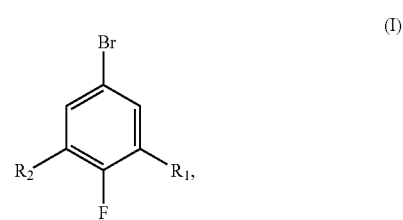

wherein
$R_1$ is halogen and $R_2$ is hydrogen or
$R_1$ is chloro and $R_2$ is halogen; comprising
a) for the preparation of a compound of formula I, wherein $R_1$ is halogen and $R_2$ is hydrogen, reacting the compound of formula II

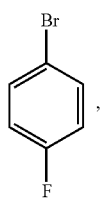
(II)

in an aprotic organic solvent in the presence of an aprotic polar co-solvent with a magnesium amide base followed by a halogenating agent, to the compound of formula I

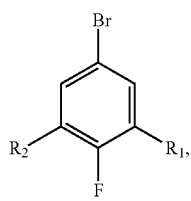
(I)

wherein $R_1$ is halogen and $R_2$ is hydrogen; and
b) for the preparation of a compound of formula I, wherein $R_1$ is chloro and $R_2$ is halogen, reacting the compound of formula I, wherein $R_1$ is chloro and $R_2$ is hydrogen, in an aprotic organic solvent in the presence of an aprotic polar co-solvent with a magnesium amide base followed by a halogenating agent to a compound of formula I, wherein $R_1$ is chloro and $R_2$ is halogen.

The following scheme describes the reactions of the invention in more detail.

Scheme 2

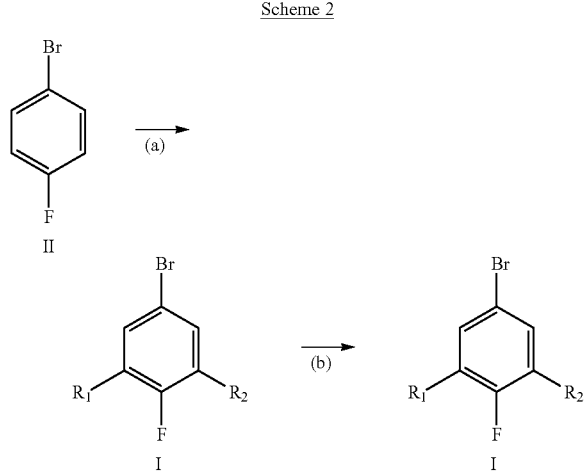

Step (a):
The compound of formula I wherein $R_1$ is halogen and $R_2$ is hydrogen can be advantageously prepared by reacting a compound of formula II first with a magnesium amide base of a formula IV

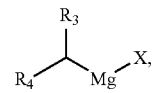
(IV)

complexed with lithium chloride;
wherein
$R_3$ and $R_4$ are, independently from each other, $C_1$-$C_6$alkyl, $C_4$-$C_7$cycloalkyl or $C_1$-$C_6$alkoxylalkyl and
X is halogen;
followed by reacting with an electrophilic halogenating agent.

Preferred compounds of formula IV are those, wherein X is Cl. Especially preferred magnesium amide bases are the compounds of formulae IVa and IVb. (free radicals represent methyl groups):

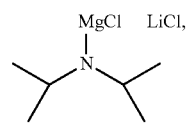
(IVa)

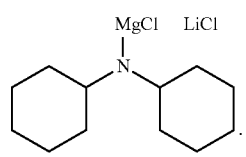
(IVb)

Suitable halogenating agents include but are not limited to chlorine, bromine, iodine, N-halogen amides such as N-chlorosuccinimide, sulfonyl chlorides such as PhSO$_2$Cl and Me$_2$NSO$_2$Cl, polyhalogenated hydrocarbons such as tetrabromomethane, hexachloroethane, Freon 113, sulfuryl chloride and hexachloroacetone. Typically the reaction is performed in an aprotic organic solvent suitable to solubilize the base. Suitable solvents include but are not limited to organic ethers such as tetrahydrofuran, 2-methyltetrahydrofuran, 1,4-dioxane, diethylether and tert.-butylmethyl ether. The most preferred solvents are tetrahydrofuran and 2-methyltetrahydrofuran.

Preferred aprotic polar co-solvents for the process of this invention show a relative permittivity (dielectric constant ∈) of above 25 at a temperature of 25° C.

Especially preferred aprotic polar co-solvents include but are not limited to phosphoramides of formula V

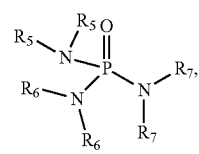
(V)

wherein $R_5$, $R_6$ and $R_7$ are, independently from each other, $C_1$-$C_6$alkyl, $C_4$-$C_7$cycloalkyl or $C_1$-$C_6$alkoxylalkyl; or $R_5$, $R_6$ or $R_7$ together form a $C_4$-$C_7$carbocycle;

cyclic ureas of formula VI

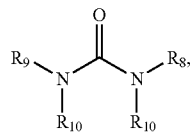
(VI)

wherein $R_8$ and $R_9$ are, independently from each other, $C_1$-$C_6$alkyl, $C_4$-$C_7$cycloalkyl or $C_1$-$C_6$alkoxylalkyl and both $R_{10}$ together form a —$CH_2$—$CH_2$— or —$CH_2$—$CH_2$—$CH_2$— chain;

an alkylated diamine of formula VII

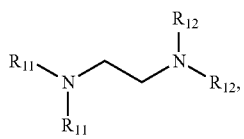
(VII)

wherein $R_{11}$ and $R_{12}$ are, independently from each other, $C_1$-$C_6$alkyl, $C_4$-$C_7$cycloalkyl or $C_1$-$C_6$alkoxylalkyl;

or both $R_{11}$ or both $R_{12}$ together form a —$CH_2$—$CH_2$—$CH_2$—$CH_2$— or —$CH_2$—$CH_2$—$CH_2$—$CH_2$—$CH_2$— chain;

In particular preferred are co-solvents of formulae Va and VIa:

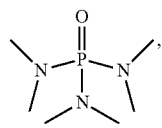
(Va)

(HMPA, $\varepsilon$ = 30)

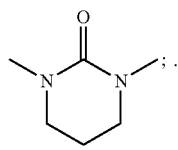
(VIa)

(DMPU, $\varepsilon$ = 36)

Free radicals represent methyl groups.

Preferably the deprotonation part of the reaction is done under continuous flow conditions allowing a minimum reaction time.

The reaction can be carried out at a temperature from –40° C. to 70° C., preferably from 0° C. to 25° C.

Step (b)

The compound of formula I wherein $R_1$ is chloro and $R_2$ is halogen can be prepared by reacting the compound of formula I wherein $R_1$ is chloro and $R_2$ is hydrogen first with a magnesium amide base of formula IV

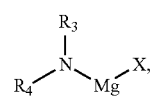
(IV)

complexed with lithium chloride;

wherein $R_3$ and $R_4$ are, independently from each other, $C_1$-$C_6$alkyl, $C_4$-$C_7$cycloalkyl or $C_1$-$C_6$alkoxylalkyl; or and X is halogen;

followed by reacting with an electrophilic halogenating agent.

Preferred compounds of formula IV are those, wherein X is Cl. Especially preferred magnesium amide bases are the compounds of formulae IVa and IVb (free radicals represent methyl groups):

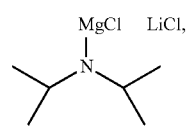
(IVa)

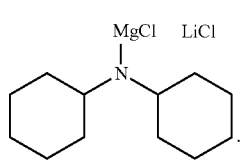
(IVb)

Suitable halogenating agents include but are not limited to chlorine, bromine, iodine, N-halogen amides such as N-chlorosuccinimide, sulfonyl chlorides such as $PhSO_2Cl$ and $Me_2NSO_2Cl$, polyhalogenated hydrocarbons such as tetrabromomethane, hexachloroethane, Freon 113, sulfuryl chloride and hexachloroacetone.

Typically the reaction is performed in an aprotic organic solvent in order to solubilize the base. Suitable solvents include but are not limited to organic ethers such as tetrahydrofuran, 2-methyltetrahydrofuran, 1,4-dioxane, diethylether and tertbutylmethyl ether. The most preferred solvents are tetrahydrofuran and 2-methyltetrahydrofuran.

Suitable aprotic polar co-solvents for the process of this invention show a relative permittivity (dielectric constant) of above 25 at a temperature of 25° C.

Suitable aprotic polar co-solvents include but are not limited to phosphoramides of formula V

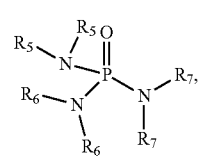
(V)

wherein $R_5$, $R_6$ and $R_7$ are, independently from each other, $C_1$-$C_6$alkyl, $C_4$-$C_7$cycloalkyl or $C_1$-$C_6$alkoxylalkyl; or $R_5$, $R_6$ or $R_7$ together form a $C_4$-$C_7$carbocycle;

cyclic ureas of formula VI

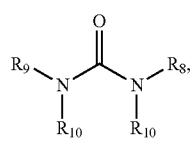

(VI)

wherein $R_8$ and $R_9$ are, independently from each other, $C_1$-$C_6$alkyl, $C_4$-$C_7$cycloalkyl or $C_1$-$C_6$alkoxylalkyl and both $R_{10}$ together form a —$CH_2$—$CH_2$— or —$CH_2$—$CH_2$—$CH_2$— chain;

alkylated diamines of formula VII

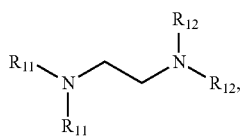

(VII)

wherein $R_{11}$ and $R_{12}$ are, independently from each other, $C_1$-$C_6$alkyl, $C_4$-$C_7$cycloalkyl or $C_1$-$C_6$alkoxylalkyl;
or both $R_{11}$ or both $R_{12}$ together represent a —$CH_2$—$CH_2$—$CH_2$—$CH_2$— or —$CH_2$—$CH_2$—$CH_2$—$CH_2$—$CH_2$— chain;

Especially preferred are aprotic polar co-solvents of formulae Va and VIa:

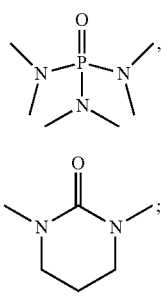

(Va)

(VIa)

Preferably the deprotonation part of the reaction is done under continuous flow conditions allowing a minimum reaction time.

The reaction can be carried out at a temperature from −40° C. to 70° C., preferably from 0° C. to 25° C.

In a preferred embodiment of the invention, the magnesium amide base of reaction steps a) and b) is identical.

In a further preferred embodiment of the invention, the aprotic organic solvent and the aprotic polar co-solvent are identical for steps a) and b).

The alkyl groups occurring in the definitions of the substituents of formula IV can be straight-chain or branched and are, for example, methyl, ethyl, n-propyl, isopropyl, n-butyl, sec-butyl, iso-butyl or tert-butyl, pentyl, hexyl and their branched isomers. Alkoxyalkyl groups preferably have a chain length of 1 to 6 carbon atoms. Alkoxyalkyl is, for example, methoxymethyl, methoxyethyl, ethoxymethyl, ethoxyethyl, n-propoxymethyl, n-propoxyethyl, iso-propoxymethyl or isopropoxyethyl. The cycloalkyl groups have from 3 to 7 ring carbon atoms, for example cyclopropyl, cyclobutyl, cyclopentyl, cyclohexyl and cycloheptyl.

PREPARATORY EXAMPLES

Example 1: Preparation of 5-bromo-1,3-dichloro-2-fluoro-benzene

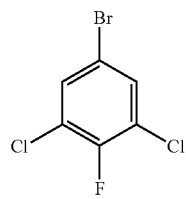

A dry, argon-flushed Schlenk-flask equipped with a magnetic stirrer and a septum was charged with 20 mL freshly titrated iPrMgCl.LiCl (1.24 M in THF, 1.0 equiv.) to which 3.8 mL of diisopropylamine (1.1 equiv.) was added dropwise at 25° C. The reaction mixture was stirred at this temperature until gas evolution was completed (ca. 48 h). The formed precipitate was dissolved with additional dry THF. The fresh solution of iPr$_2$NMgCl.LiCl in THF was titrated at 25° C. with benzoic acid and 4-(phenylazo)diphenylamine as an indicator. A concentration of 0.59 M was obtained.

To a solution of 4-bromo-2-chloro-1-fluoro-benzene (0.209 g, 1.00 mmol) in THF (1 mL) was added iPr$_2$NMgCl.LiCl (0.59 M, 3.39 ml, 2.00 mmol) at 25° C. and the resulting mixture was stirred for 15 min at 25° C. Hexachloro-2-propanone (0.397 g, 1.50 mmol) was added at 0° C. and the mixture was stirred for 15 min. The resulting mixture was then quenched with sat. aq. NH$_4$Cl, extracted with ethyl acetate and dried over anhydrous Na$_2$SO$_4$. After filtration, the solvent was removed in vacuo. Quantitative GC measurement showed that the ratio between 5-bromo-1,3-dichloro-2-fluoro-benzene and regioisomer is about 12:1. Purification by flash column chromatography (SiO$_2$, i-hexane) furnished 5-bromo-1,3-dichloro-2-fluoro-benzene (0.190 g) as a colorless oil.

Diisopropylamine (3.1 ml, 21 mmol) was added dropwise to 1.3 M iPrMgCl.LiCl in THF (15.0 ml, 19.5 mmol) and the resulting suspension was stirred at ambient temperature for 20 h. DMPU (1.5 ml, 12 mmol) was added resulting in a clear solution. The fresh solution of iPr$_2$NMgCl.LiCl in THF with DMPU as an additive was titrated at 25° C. with benzoic acid and 4-(phenylazo)diphenylamine as an indicator. A concentration of 1.10 M was obtained.

To a solution of 4-bromo-2-chloro-1-fluoro-benzene (0.993 g, 4.74 mmol) in THF (4.7 mL) was added the solution of iPr$_2$NMgCl.LiCl (1.10 M, 4.70 ml, 5.21 mmol) prepared above at ambient temperature and the resulting mixture was stirred for 20 min. This reaction mixture was added dropwise to a solution of hexachloroacetone (1.90 g, 7.11 mmol) in THF (2 ml) and stirring was continued for 15 min. Quantitative LC/MS analysis using decafluorobiphenyl as an internal standard indicated that the reaction mixture contains 5-bromo-1,3-dichloro-2-fluoro-benzene (0.957 g) and 4-bromo-2-chloro-1-fluoro-benzene (0.150 g). No regioisomeric product was observed under these conditions.

It is clear from the experiments above that the addition of a polar aprotic additive provides an advantage in doing the reaction using only an easily available magnesium base since it provides an improved regioselectivity and avoids the use of large excess of base (1.1 eq vs 2.0 eq without additive). In addition higher concentration of the reaction media was achieved which is beneficial for production on a large scale.

Preparation of 5-bromo-1,3-dichloro-2-fluoro-benzene under flow conditions

The flow system (FlowSyn, Uniqsis) was dried by flushing it with dry THF (flow rate of all pumps: 1.00 mL/min; run-time: 30 min). Injection loop A was loaded with 4-bromo-2-chloro-1-fluorobenzene (0.425 g, 2.03 mmol, 1.00 M in dry THF+10 vol % DMPU; 3.0 mL) and injection loop B was loaded with (Magnesium Diisopropyl Amide) .LiCl (1.10 M in dry THF+10 vol % DMPU; 2.23 mmol, 3.0 mL). The solutions were simultaneously injected into separate THF streams (pump A and B; flow rates: 0.25 mL/min each) and mixed in a T-shaped tube connector. The combined streams passed a coiled and a tube reactor (2.5 mL; residence time: 5 min; 25° C.) and were collected in a dry, argon-flushed flask equipped with a magnetic stirrer and a septum containing hexachloroacetone (2.03 M in dry THF, 1.10 mL; 2.23 mmol). After collecting the magnesiated intermediate, the pumps were turned off and the reaction mixture was stirred for additional 1.5 h. The reaction was quenched with sat. aq. NH$_4$Cl (30 mL) and the aq. layer was extracted with EtOAc (3×40 mL). The combined organic fractions were dried over anhydrous Na$_2$SO$_4$, filtrated and the solvent was removed in vacuo. Purification by flash column chromatography (SiO$_2$, i-hexane) furnished a colorless oil (0.440 g) containing 5-bromo-1,3-dichloro-2-fluoro-benzene as well as approx. 10% of 4-bromo-2-chloro-1-fluorobenzene. No regioisomeric product was observed under these conditions.

Example 2: Preparation of 5-bromo-1-chloro-2-fluoro-3-iodo-benzene

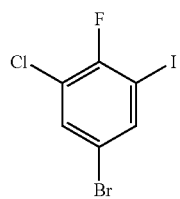

To a solution of 2,2,6,6-tetramethylpiperidine (0.266 g, 1.86 mmol) in THF (4.3 ml) was added dropwise at −20° C. n-butyllithium in hexanes (2.5M, 0.69 ml, 1.72 mmol). The reaction media was stirred at −20° C. for 15 min before being cooled down to −78° C. 4-bromo-2-chloro-1-fluorobenzene (0.300 g, 1.43 mmol) was added dropwise and stirring was continued for 2 h. Then a solution of iodine (0.40 g, 1.58 mmol) in THF (1.4 ml) was added dropwise. After stirring for another 10 min the reaction was quenched with aq NaHCO$_3$ and the aqueous layer was extracted with cyclohexane (3×). The combined organic layers were dried over anhydrous Na$_2$SO$_4$ and evaporated under reduced pressure. Analysis of the crude mixture by quantitative 1H NMR using trimethoxy benzene as an internal standard gave 53% of 5-bromo-1-chloro-2-fluoro-3-iodo-benzene, 32% of regioisomer containing one iodine, 11.5% of starting material and 3.6% of byproduct containing two iodines.

This preparatory example demonstrates that a use of strong lithium bases such as lithium tetramethylpiperidine (LiTMP) is not suitable for obtaining compounds of formula I when R$_2$ is chloro in high yield and regioselectivity.

The invention claimed is:

1. A process for the preparation of a compound of formula I

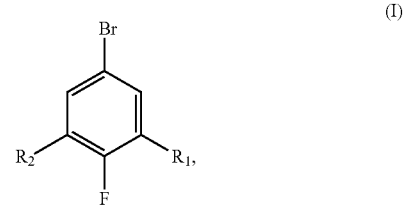

wherein

R$_1$ is halogen and R$_2$ is hydrogen or

R$_1$ is chloro and R$_2$ is halogen; comprising a) for the preparation of a compound of formula I, wherein R$_1$ is halogen and R$_2$ is hydrogen, reacting the compound of formula II

in an aprotic organic solvent in the presence of an aprotic polar co-solvent, different from the aprotic organic solvent, with a magnesium amide base followed by a halogenating agent, to the compound of formula I

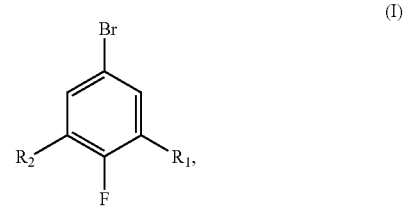

wherein R$_1$ is halogen and R$_2$ is hydrogen; and b) for the preparation of a compound of formula I, wherein R$_1$ is chloro and R$_2$ is halogen, reacting the compound of formula I, wherein R$_1$ is chloro and R$_2$ is hydrogen, in an aprotic organic solvent in the presence of an aprotic polar co-solvent, different from the aprotic organic solvent, with a magnesium amide base followed by a halogenating agent to a compound of formula I, wherein R$_1$ is chloro and R$_2$ is halogen.

2. A process according to claim 1, characterized in that in step a) the magnesium amide base is a compound of formula IV

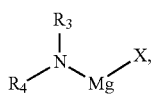

(IV)

complexed with lithium chloride;
wherein
$R_3$ and $R_4$ are, independently from each other, $C_1$-$C_6$alkyl, $C_4$-$C_7$cycloalkyl or $C_1$-$C_6$alkoxylalkyl;
and X is halogen.

3. A process according to claim 1, characterized in that in step b) the magnesium amide base is a compound of formula IV

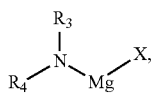

(IV)

complexed with lithium chloride;
wherein
$R_3$ and $R_4$ are, independently from each other, $C_1$-$C_6$alkyl, $C_4$-$C_7$cycloalkyl or $C_1$-$C_6$alkoxylalkyl;
and X is halogen.

4. A process according to claim 1, characterized in that the magnesium amide base of reaction steps a) and b) is identical.

5. A process according to claim 1, characterized in that the aprotic polar co-solvent in reaction step a) is selected from the group consisting of the compounds of formula V

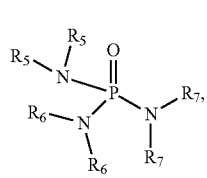

(V)

wherein $R_5$, $R_6$ and $R_7$ are, independently from each other, $C_1$-$C_6$alkyl, $C_4$-$C_7$cycloalkyl or $C_1$-$C_6$alkoxylalkyl; or $R_5$, $R_6$ or $R_7$ together form a $C_4$-$C_7$carbocycle;
the compounds of formula VI

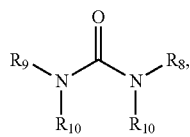

VI)

wherein $R_8$ and $R_9$ are, independently from each other, $C_1$-$C_6$alkyl, $C_4$-$C_7$cycloalkyl or $C_1$-$C_6$alkoxylalkyl and both $R_{10}$ together represent a —$CH_2$—$CH_2$— or —$CH_2$—$CH_2$—$CH_2$— chain;

and the compounds of formula VII

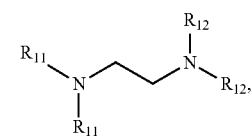

(VII)

wherein $R_{11}$ and $R_{12}$ are, independently from each other, $C_1$-$C_6$alkyl, $C_4$-$C_7$cycloalkyl or $C_1$-$C_6$alkoxylalkyl;
or both $R_{11}$ or both $R_{12}$ together represent a —$CH_2$—$CH_2$—$CH_2$—$CH_2$— or —$CH_2$—$CH_2$—$CH_2$—$CH_2$—$CH_2$-chain.

6. A process according to claim 1, characterized in that the aprotic polar co-solvent in reaction step b) is selected from the group consisting of the compounds of formula V

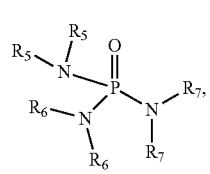

(V)

wherein $R_5$, $R_6$ and $R_7$ are, independently from each other, $C_1$-$C_6$alkyl, $C_4$-$C_7$cycloalkyl or $C_1$-$C_6$alkoxylalkyl; or $R_5$, $R_6$ or $R_7$ together form a $C_4$-$C_7$carbocycle;
the compounds of formula VI

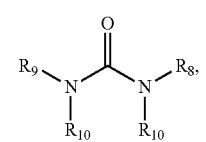

VI)

wherein $R_8$ and $R_9$ are, independently from each other, $C_1$-$C_6$alkyl, $C_4$-$C_7$cycloalkyl or $C_1$-$C_6$alkoxylalkyl and both $R_{10}$ together represent a —$CH_2$—$CH_2$— or —$CH_2$—$CH_2$—$CH_2$— chain;
and the compounds of formula VII

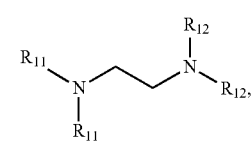

(VII)

wherein $R_{11}$ and $R_{12}$ are, independently from each other, $C_1$-$C_6$alkyl, $C_4$-$C_7$cycloalkyl or $C_1$-$C_6$alkoxylalkyl; or both $R_{11}$ or both $R_{12}$ together represent a —$CH_2$—$CH_2$—$CH_2$—$CH_2$— or —$CH_2$—$CH_2$—$CH_2$—$CH_2$—$CH_2$— chain.

7. A process according to claim 1, characterized in that the halogenating agent in step a) is chlorine, bromine, iodine, N-halogen amides, sulfonyl chlorides, polyhalogenated hydrocarbons, sulfuryl chloride or hexachloroacetone.

8. A process according to claim 1, characterized in that the halogenating agent in step b) is chlorine, bromine, iodine, N-halogen amides, sulfonyl chlorides, polyhalogenated hydrocarbons, sulfuryl chloride or hexachloroacetone.

9. A process according to claim 1, characterized in that the aprotic organic solvent and the aprotic polar co-solvent are identical for steps a) and b).

10. A process according to claim 1, comprising
  a) reacting the compound of formula II

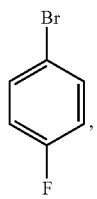

(II)

in an aprotic organic solvent comprising organic ethers in the presence of an aprotic polar co-solvent selected from the group consisting of compounds of formulae Va and VIa

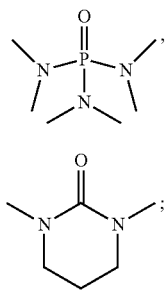

(Va)

(VIa)

with a magnesium amide base selected from the group consisting of compounds of formulae IVa and IVb,

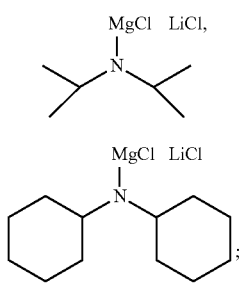

(IVa)

(IVb)

followed by a halogenating agent selected from chlorine, bromine, iodine, N-halogen amides, sulfonyl chlorides, polyhalogenated hydrocarbons, sulfuryl chloride and hexachloroacetone;
  to the compound of formula I, wherein $R_1$ is halogen and $R_2$ is hydrogen

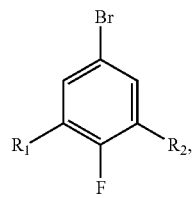

(I)

and
  b) reacting the compound of formula I wherein $R_1$ is chloro and $R_2$ is hydrogen in an aprotic organic solvent comprising organic ethers in the presence of an aprotic polar co-solvent selected from the group consisting of compounds of formulae Va and VIa

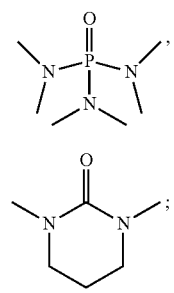

(Va)

(VIa)

with a magnesium amide base selected from the group consisting of compounds of formulae IVa and IVb,

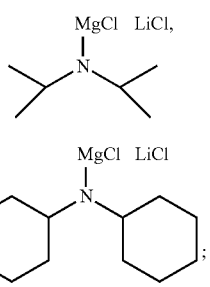

(IVa)

(IVb)

followed by a halogenating agent selected from the group consisting of chlorine, bromine, iodine, N-halogen amides, sulfonyl chlorides, polyhalogenated hydrocarbons, sulfuryl chloride and hexachloroacetone; to a compound of formula I, wherein $R_1$ is chloro and $R_2$ is halogen.

* * * * *